United States Patent
Tekulve et al.

(10) Patent No.: US 11,780,623 B2
(45) Date of Patent: Oct. 10, 2023

(54) FLAT WIRE COIL WIRE GUIDE WITH TWISTED CONTRACTION

(71) Applicant: Cook Medical Technologies LLC, Bloomington, IN (US)

(72) Inventors: Kurt J. Tekulve, Ellettsville, IN (US); Andrew Bowers, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1294 days.

(21) Appl. No.: 16/251,275

(22) Filed: Jan. 18, 2019

(65) Prior Publication Data

US 2019/0248523 A1    Aug. 15, 2019

Related U.S. Application Data

(60) Provisional application No. 62/631,049, filed on Feb. 15, 2018.

(51) Int. Cl.
*B65B 27/06*     (2006.01)
*B21C 47/24*    (2006.01)
(Continued)

(52) U.S. Cl.
CPC ............ *B65B 27/06* (2013.01); *A61M 25/09* (2013.01); *A61M 25/09033* (2013.01);
(Continued)

(58) Field of Classification Search
CPC .... A61M 5/00; A61M 25/00; A61M 25/0009; A61M 25/0012; A61M 25/09; A61M 25/09016; A61M 25/09025; A61M 25/09033; A61M 2025/09058; A61M 2025/09108; A61M 2025/09175;
(Continued)

(56) References Cited

U.S. PATENT DOCUMENTS 3,548,739 A    3/1969  Glasson et al.
4,080,706 A    3/1978  Heilman et al.
(Continued)

FOREIGN PATENT DOCUMENTS

JP    2004208704 A  *  7/2004
JP    2011143077        7/2011
(Continued)

OTHER PUBLICATIONS

Machine Translation of JP-2004208704-A, patents.google.com, 7 pages, printed on Nov. 17, 2022. (Year: 2022).*
(Continued)

*Primary Examiner* — Matthew Kremer
(74) *Attorney, Agent, or Firm* — Liell + McNeil

(57) ABSTRACT

A wire guide includes a solid core mandrel that is initially received in a flat wire coil that has a rest inner diameter that is greater than a uniform diameter of the solid core mandrel. The flat wire of the flat wire coil is in tension between a proximal location and a distal location so that the flat wire coil has a reduced inner diameter that is smaller than its rest inner diameter. The tension in the flat wire is introduced by torquing the mandrel relative to the flat wire coil as part of attaching the coil to the mandrel.

15 Claims, 2 Drawing Sheets

(51) Int. Cl.
*A61M 25/09* (2006.01)
*B21F 15/00* (2006.01)

(52) U.S. Cl.
CPC .............. *B21C 47/24* (2013.01); *B21F 15/00* (2013.01); *A61M 2025/09083* (2013.01); *A61M 2025/09108* (2013.01); *A61M 2025/09175* (2013.01)

(58) Field of Classification Search
CPC ......... A61M 2025/09191; A61M 2025/09133; A61M 2025/09083; A61F 2/9526
See application file for complete search history.

(56) References Cited

U.S. PATENT DOCUMENTS

| | | | |
|---|---|---|---|
| 4,748,986 A * | 6/1988 | Morrison | A61M 25/09033 604/170.01 |
| 4,932,419 A | 6/1990 | de Toledo | |
| 5,147,317 A * | 9/1992 | Shank | A61M 25/09 604/528 |
| 5,203,772 A * | 4/1993 | Hammerslag | A61M 25/0144 604/95.04 |
| 5,299,580 A | 4/1994 | Atkinson et al. | |
| 5,433,200 A | 7/1995 | Fleischhacker, Jr. | |
| 5,700,253 A | 12/1997 | Parker | |
| 2007/0162108 A1 * | 7/2007 | Carlson | A61M 25/09 623/901 |
| 2008/0045908 A1 * | 2/2008 | Gould | A61M 25/09 604/272 |
| 2008/0200839 A1 | 8/2008 | Bunch et al. | |
| 2014/0180028 A1 | 6/2014 | Burkett | |
| 2015/0259131 A1 | 9/2015 | Weissbrod | |
| 2021/0220613 A1 * | 7/2021 | von Segesser | A61M 25/09025 |

FOREIGN PATENT DOCUMENTS

| | | | |
|---|---|---|---|
| JP | 201589379 | | 5/2015 |
| JP | 2016174645 A | * | 10/2016 |

OTHER PUBLICATIONS

Machine Translation of JP-2016174645-A, patents.google.com, 7 pages, printed on Nov. 22, 2022. (Year: 2022).*

European Patent Office, European Search Report for Application No. 1915409.1-1132, dated Jul. 15, 2019, Munich, Germany.

Harrison et al., Guidewire Stiffness: What's in a Name?, Journal of Endovascular Therapy, 2011; 18:797-801, by the International Society of Endovascular Specialists, Dec. 2011, pp. 797-801, Liverpool, UK.

* cited by examiner

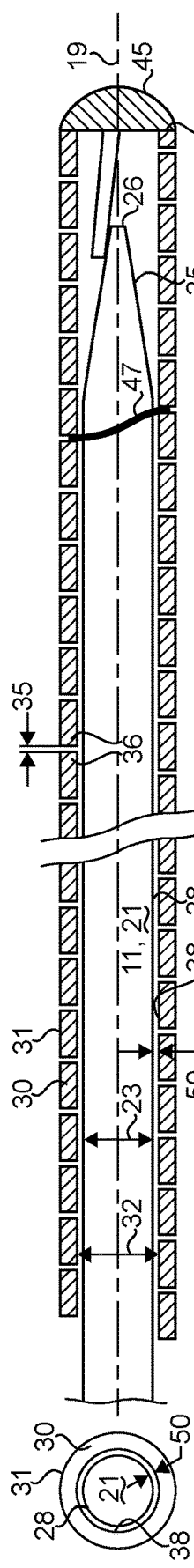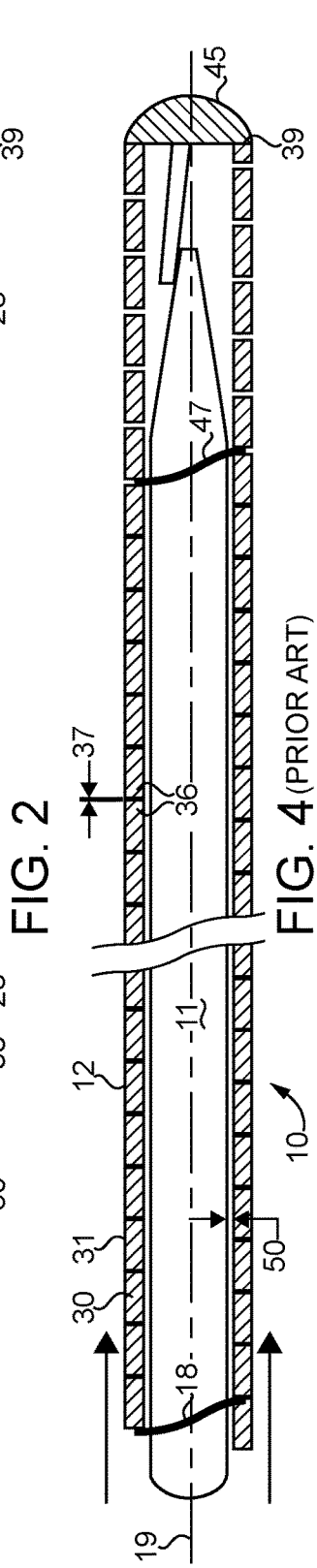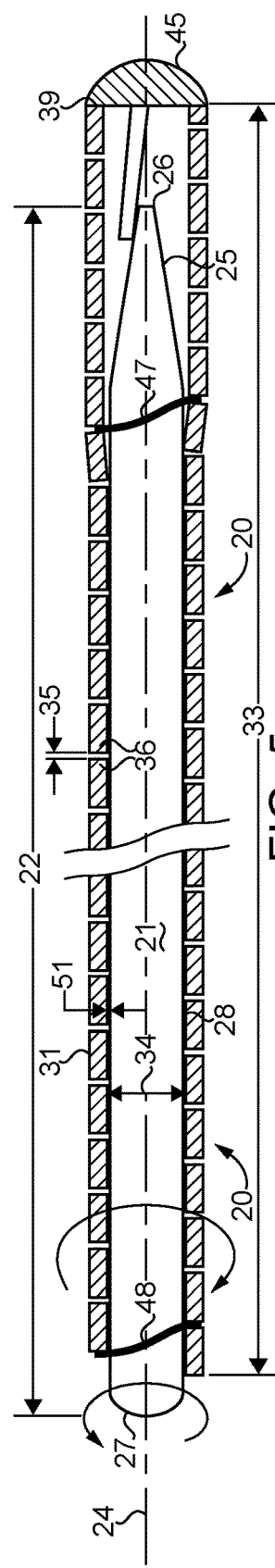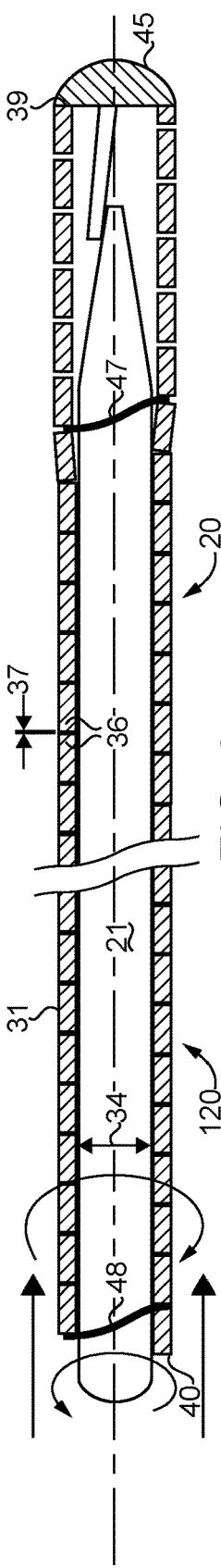

FLAT WIRE COIL WIRE GUIDE WITH TWISTED CONTRACTION

TECHNICAL FIELD

The present disclosure relates generally to wire guides that include both a solid core and an outer coil, and is directed specifically to a twist contraction strategy for mating a flat wire coil to a solid core mandrel of a wire guide.

BACKGROUND

One class of wire guides 10 as shown in FIG. 1, include a solid core mandrel 11 that is received in, and attached to, a flat wire coil 12. This type of wire guide 10 is typically made by sliding the mandrel 11 into a previously made coil 12. The coil 12 and mandrel 11 are then joined at a distal attachment location. Next, the coil 12 is compressed from its proximal end toward its distal end before, or contemporaneously with, making an attachment at a proximal attachment location. Because the coil 12 must inherently have an internal diameter in its rest shape that is greater than an outer diameter of the mandrel, the radial gap between the outer surface of the mandrel and the internal surface of the coil can, on rare occasions, result in the coil jumping 13 at one or more locations when the completed wire guide is wound and packaged, as shown in FIG. 1. Although this phenomenon is rare, the wire guide may not be usable, as the coil jumping 13 may not rectify itself when the wire guide 10 is unpackaged from package 14 and unwound from loop 15 for use.

The present disclosure is directed toward one or more of the problems set forth above.

SUMMARY

In one aspect, a wire guide includes an elongated solid core mandrel with a length, and a uniform diameter over a majority of the length. A flat wire is formed into a flat wire coil that, when at rest, defines a rest inner diameter that is greater than the uniform diameter of the mandrel. The flat wire coil has a coil length that matches the length of the elongated solid core mandrel. The elongated solid core mandrel is received in the flat wire coil. The flat wire coil is attached to the elongated solid core mandrel at a distal attachment location and a proximal attachment location. The distal attachment location is closer to a distal end of the elongated solid core mandrel than to the proximal attachment location, which is closer to the proximal end of the elongated solid core mandrel than to the distal attachment location. The flat wire is in tension between the proximal attachment location and the distal attachment location so that the flat wire coil has a reduced inner diameter, which is smaller than the rest inner diameter, between the proximal attachment location and the distal attachment location.

In another aspect, a method of making a wire guide includes sliding an elongate solid core mandrel into a flat wire coil. The flat wire coil is attached to the elongate solid core mandrel at a distal attachment location. The elongate solid core mandrel is torqued in a direction with respect to the flat wire coil that puts tension in a flat wire of the flat wire coil, and reduces an inner diameter of the flat wire coil from a rest inner diameter to a reduced inner diameter. The flat wire coil is attached to the elongate solid core mandrel at a proximal attachment location while retaining the tension in the flat wire. The distal attachment location is closer to a distal end in the elongate solid core mandrel than to the proximal attachment location, which is closer to the proximal end of the elongate solid core mandrel than to the distal attachment location.

BRIEF DESCRIPTION OF THE DRAWINGS

FIG. 2 is a schematic side view of a step in the construction of a wire guide according to the present disclosure;

FIG. 3 is a schematic end view of the partially completed wire guide of FIG. 2;

FIG. 4 is a schematic side view of a wire guide according to the prior art;

FIG. 5 is a schematic side view of a wire guide according to the present disclosure; and FIG. 6 is a schematic side view of a wire guide according to another aspect of the present disclosure.

DETAILED DESCRIPTION

Figure 1:
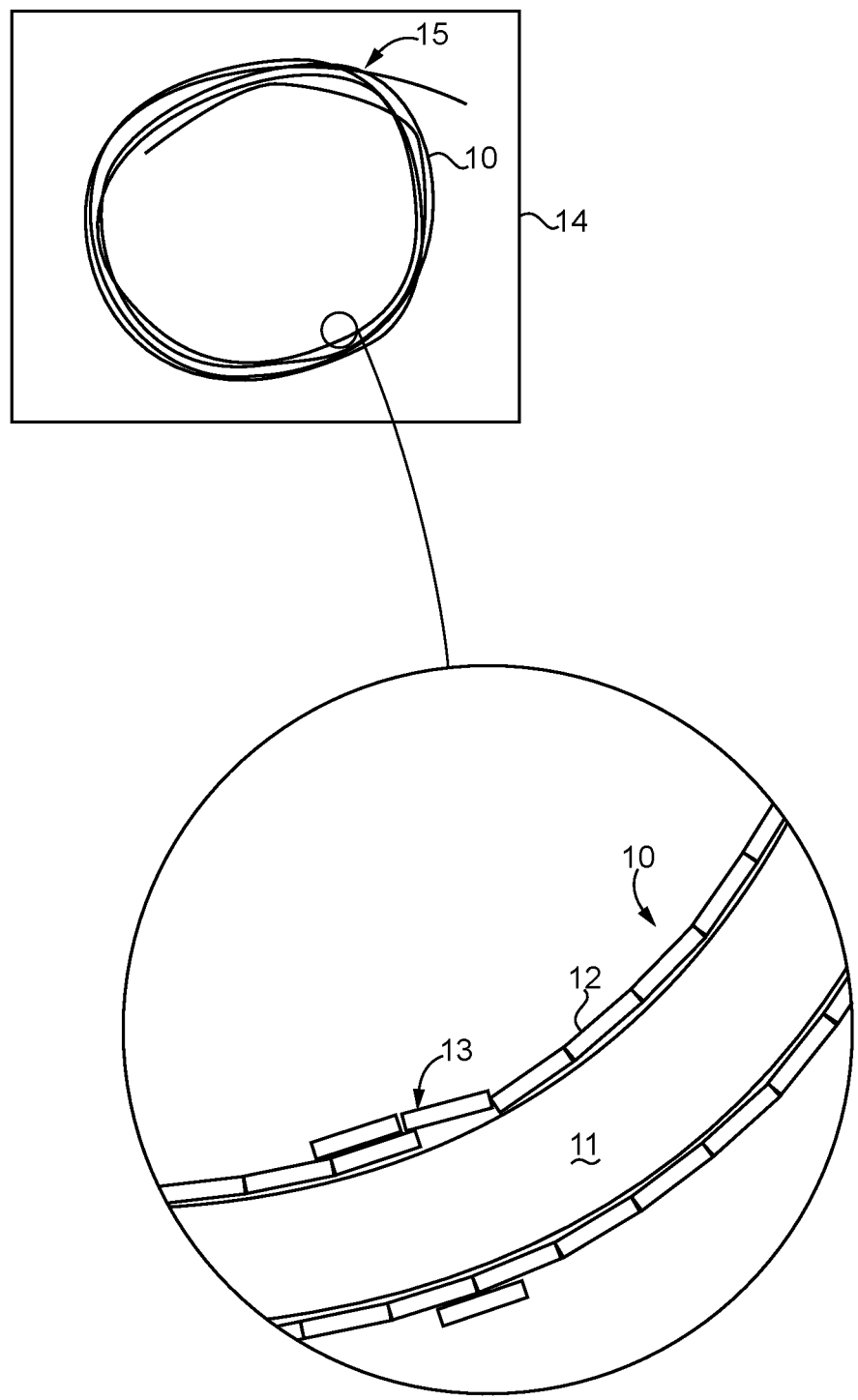
FIG. 1 is a schematic view of a packaged wire guide and an enlargement showing a coil jump problem addressed by the present disclosure.

Referring now to FIGS. 2 and 3, all wire guides according to the present disclosure are constructed by sliding an elongated solid core mandrel 21 into a flat wire coil 31. Thus, both the flat wire coil 31 and the solid core mandrel 21 existed apart from each other prior to being mated as shown in FIG. 2. Mandrel 21 may include a distal tapered segment 25 that terminates at a distal end 26 attached to a rounded cap 45, which is also attached to a distal end 39 of flat wire coil 31, such as by solder or welding. Flat wire coil 31 may be attached to solid core mandrel 21 with a solder at a distal attachment location 47, which may typically be located proximal to the distal tapered segment 25. Those skilled in the art will appreciate that coil 31 could be attached to mandrel 21 by any suitable manner known in the art without departing from the present disclosure. These attachment strategies include, but are not limited to, weld, solder, glue, crimp, laser attachment, etc. Those skilled in the art will appreciate that in order to slide mandrel 21 into flat wire coil 31, flat wire coil 31 must inherently define a rest inner diameter 32, when at rest, that is greater than a uniform diameter 23 of a majority of the length of the solid core mandrel 21. At this stage in manufacture, the mandrel 21 may not have yet had its proximal end cut and rounded so that the mandrel 21 has a matching length with the flat wire coil 31. In FIGS. 2 and 3, the diametrical difference between the inner diameter 32 of flat wire coil 31 and the outer diameter 23 of mandrel 21 is shown in exaggeration by the radial gap 50 between the external surface 28 of mandrel 21 and the inner surface 38 of flat wire coil 31. Gap 50, when flat wire coil 31 is at rest, may be typically less than one order of magnitude smaller than diameter 23. In addition to radial gap 50, flat wire coil 31, again while at rest, defines a rest winding gap 35 between adjacent turns 36 of the flat wire coil 31. This winding gap may typically be less than one order of magnitude smaller than a cross sectional width of flat wire 30. In all cases of the present disclosure, flat wire coil 31 is formed from a flat wire 30. The term "flat wire" means a cross section that includes at least three orthogonal surfaces, with two of those orthogonal surfaces being in parallel and facing one another in adjacent turns 36 of coil 31, and the third orthogonal surface defining the inner surface 38 of coil 31. In the illustrated embodiment, the flat wire coil 31 has a rectangular cross section with a major axis oriented in parallel with a longitudinal axis 19 of flat wire coil 31. Nevertheless, those skilled in the art will appreciate that a flat wire coil according to the present disclosure could have cross sectional shapes that differ from that shown without departing from the intended scope of the present disclosure. For instance, the outer surface of the flat wire 30 could be convex and rounded.

Referring now to FIG. 1 and FIG. 4, a prior art wire guide 10 is transformed from the partial construction of FIGS. 2 and 3 by compressing flat wire coil 31 along longitudinal axis 19 in the direction of distal attachment location 47 to reduce the winding gap from the rest winding gap 35 of FIG. 2 to a reduced winding gap 37, which is smaller than the rest winding gap 35. In practice, the reduced winding gap 37 approaches zero. The compression in a flat wire coil 31 is maintained via a second attachment of flat wire coil 31 to the underlying mandrel 11 at a proximal attachment location 18. Thus, if one were to break attachment 18, one could expect flat wire coil 31 to expand in length along longitudinal axis 19, but not tend to unwind when returning to a rest geometry as per FIG. 2. Because the coil 31 is only compressed, the radial gap 50 between the outer surface of mandrel 11 and the inner surface of flat wire coil 31 is not substantially altered. It is believed that this radial gap 50 contributes to the phenomenon of the coil sometimes jumping, such as when the wire guide 10 is wound for packaging as shown in FIG. 1. Those skilled in the art will appreciate that the compression of the flat wire coil 31 substantially increases the stiffness of a wire guide relative to one in which a flat wire coil was attached proximally while still in a rest shape.

Referring now to FIG. 5, the present disclosure teaches an alternative strategy for increasing stiffness and mating the flat wire coil 31 to the underlying mandrel 21 to produce a completed wire guide 20 according to the present disclosure. Instead of compressing flat wire coil 31 along the longitudinal axis 19, the flat wire coil 31 is instead torqued about longitudinal axis 24 with regard to mandrel 21. The flat wire coil 31 responds by the flat wire 30 going into tension, and the flat wire coil 31 contracting to a reduced inner diameter 34, which is smaller than the rest inner diameter 32. This results in a reduced radial gap 51, which is smaller than rest radial gap 50. The tension in flat wire 30 is maintained by attachment of flat wire coil 31 to mandrel 21 at proximal attachment location 48. Those skilled in the art will appreciate that coil 31 could be attached at proximal location 48 to mandrel 21 by any suitable manner known in the art without departing from the present disclosure. These attachment strategies include, but are not limited to, welding, solder, glue, crimp, laser attachment, etc. After this is made, the mandrel 21 may be cut to a matching length with flat wire coil 31 and then rounded at a proximal end 27 in a manner known in the art.

If one were to break the attachment at proximal attachment location 48, a wire guide 20 according to the present disclosure would be revealed by the flat wire coil 31 unwinding to release the stored tension in the flat wire 30. This is to be contrasted with the prior art wire guide 10 of FIG. 4. In general, a wire guide 20 according to the present disclosure includes a mandrel 21 having a length 22 that matches a length 33 of the flat wire coil 31. Matching lengths in the context of wire guides according to the present disclosure does not necessarily mean equal, but does mean that a ratio of the two lengths when rounded to a single significant digit would be the numeral 1. Those skilled in the art will appreciate that, because the mandrel 21 and flat wire coil 31 are torqued relative to one another, the resulting winding gap 35 may undergo little to no substantial change from the rest winding gap 35 associated with the unstressed flat wire coil 31 of FIG. 2. By having the inner surface of flat wire coil 31 tightened down closer to the outer surface 28 of mandrel 21, the resulting wire guide 20 is relatively stiff, and maybe even more stiff than counterpart wire guide 10. However, the torqueing strategy that results in stored tension in the flat wire 30 according to the embodiment of FIG. 5, may reduce the likelihood of the coil jumping phenomenon when the completed wire guide is wound on itself for packaging as shown in FIG. 1.

Referring now to FIG. 6, a wire guide 20 according to the present disclosure always includes the relative torqueing and stored tension in wire 30 illustrated with regard to FIG. 5, but may also in addition include the coil compression strategy associated with the prior art of FIG. 4. Thus, both strategies may be employed to both produce a flat wire coil 31 with a reduced inner diameter 34, which is less than the rest inner diameter 32 (FIG. 2) and also a reduced winding gap 37, which is smaller than the rest winding gap 35 (FIG. 2). Thus, prior to or contemporaneously with the application of the attachment at proximal attachment location 48, the flat wire coil 31 is both torqued with respect to the underlying mandrel 21, and also compressed along longitudinal axis 24 in the direction of distal attachment location 47.

A wire guide 20 according to the present disclosure includes an elongated solid core mandrel 21 with a length 22, and a uniform diameter 23 over a majority of the length 22. A flat wire 30 is formed into a flat wire coil that, when at rest, defines a rest inner diameter 32 that is greater than the uniform diameter 23, and has a coil length 33 that matches the length 22 of the elongated solid core mandrel 21. The elongated solid core mandrel 21 is received in the flat wire coil 31, which is to be contrasted with a flat wire coil actually formed on an underlying mandrel. The flat wire coil 31 is attached to the elongated solid core mandrel 21 at a distal attachment location 47 and a proximal location 48. The distal attachment location 47 is closer to a distal end 26 of the elongated solid core mandrel 21 than to the proximal attachment location 48, which is closer to the proximal end 27 of the elongated solid core mandrel 21 than to the distal attachment location 47. In other words, in most instances, the vast majority of the length of the wire guide will exist between the distal attachment location 47 and the proximal attachment location 48. The flat wire 30 is held in tension between the proximal attachment location 48 and the distal attachment location 47 so that the flat wire coil 31 has a reduced inner diameter 34, which is smaller than the rest inner diameter 32, between the proximal attachment location 48 and the distal attachment location 47. In the case of the super stiff embodiment of FIG. 6, the flat wire coil 31 is also compressed between the proximal attachment location 48 and the distal attachment location 47 so as to define a reduced winding gap 37, which is smaller than the rest winding gap 35 associated with the partially completed wire guide of FIG. 2.

INDUSTRIAL APPLICABILITY

The present disclosure finds generally applicability in wire guides, and finds specific application to a class of wire guides that include a flat wire coil surrounding a solid core mandrel. A flat wire coil according to the present disclosure always means something other than a coil formed from a wire having a round or oval cross section. The present disclosure finds specific applicability to a class of relatively stiff wire guides often associated with a previous inventor by the name of Amplatz. Some wire guides according to the present disclosure may generally be referred to as Amplatz type wire guides.

A wire guide 20 according to the present disclosure may be made by initially sliding an elongated solid core mandrel 21 into a flat wire coil 31. The flat wire coil 31 may then be soldered to the elongated solid core mandrel 21 at a distal attachment location 47. The elongated solid core mandrel is torqued in a direction with respect to the flat wire coil 31 that puts tension in the flat wire 30 of the flat wire coil 31, and reduces an inner diameter of the flat wire coil 31 from a rest inner diameter 32 to a reduced inner diameter 34. Those skilled in the art will appreciate that the construction process may be standardized by arriving at a predetermined range of torque stress, which can be measured, to standardize the procedure and achieve consistent results. The flat wire coil 31 is attached to the elongated solid core mandrel 21 at the proximal attachment location 48 contemporaneously with or after the torqueing step to retain the tension in the flat wire 30. In the case of the embodiment of FIG. 6, the torqueing step may also include a compression step by moving a proximal end 40 of the flat wire coil 31 relative to the solid core mandrel 21 in a direction toward the distal attachment location 47 along longitudinal axis 24. The amount of movement will be small as it amounts to an accumulative reduction in the winding gap 35 between adjacent turns 36 of flat wire coil 31. Also in the case of the embodiment of FIG. 6, the torqueing and compressing steps may be performed contemporaneously with each other, and may be contemporaneously with the application of attachment or solder material to complete proximal attachment location 48. The soldering at proximal attachment location 48 may include positioning hot liquid solder material in a winding gap defined between the proximal two turns 36 of flat wire coil 31. Preferably, the torqueing step would be stopped at a pre-determined torque magnitude, and then the stress resulting from the torqueing step would be stored in the tension of the flat wire 30. In general, wire guides 20 according to the present disclosure are believed to be made stiffer by increasing interference contact between the solid core mandrel 21 and the flat wire coil 31. This interference contact is believed to be increased responsive to the torqueing step. In all wire guides 20 according to the present disclosure, one could expect lesser numbers of coil jump phenomenon associated with rare occurrences when the wire guide is wound on itself for packaging.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:

1. A wire guide comprising:
    an elongated solid core mandrel with a length, and a uniform diameter over a majority of the length;
    a flat wire formed into a flat wire coil that, when at rest, defines a rest inner diameter that is greater than the uniform diameter, and an entire coil length of the flat wire coil matches the length of the elongated solid core mandrel;
    the elongated solid core mandrel being received in the flat wire coil;
    the flat wire coil being attached to the elongated solid core mandrel at a distal attachment location and a proximal attachment location;
    the distal attachment location being closer to a distal end of the elongated solid core mandrel than to the proximal attachment location, which is closer to a proximal end of the elongated solid core mandrel than to the distal attachment location;
    wherein the flat wire is in tension between the proximal attachment location and the distal attachment location so that the flat wire coil has a reduced inner diameter, which is smaller than the rest inner diameter, between the proximal attachment location and the distal attachment location, and such that a winding gap between adjacent turns of the flat wire coil is unchanged from a rest winding gap of the flat wire coil when at rest.

2. The wire guide of claim 1 wherein the flat wire has a rectangular cross section.

3. The wire guide of claim 1 wherein the elongated solid core mandrel terminates with a distal tapered segment; and
    the distal attachment location is proximal to the distal tapered segment.

4. The wire guide of claim 1 including a rounded cap attached to a distal end of the flat wire coil and attached to the distal end of the elongated solid core mandrel.

5. The wire guide of claim 1 wherein the tension in the flat wire corresponds to a predetermined range of torque stress between the elongated solid core mandrel and the flat wire coil about a common longitudinal axis.

6. The wire guide of claim 1 wherein a radial gap between an external surface of the elongated core mandrel and an inner surface of the flat wire coil is less than one order of magnitude smaller than the uniform diameter.

7. A wire guide comprising:
    an elongated solid core mandrel with a length, and a uniform diameter over a majority of the length;
    a flat wire formed into a flat wire coil that, when at rest, defines a rest inner diameter that is greater than the uniform diameter, and an entire coil length of the flat wire coil matches the length of the elongated solid core mandrel;
    the elongated solid core mandrel being received in the flat wire coil;
    the flat wire coil being attached to the elongated solid core mandrel at a distal attachment location and a proximal attachment location;
    the distal attachment location being closer to a distal end of the elongated solid core mandrel than to the proximal attachment location, which is closer to a proximal end of the elongated solid core mandrel than to the distal attachment location;
    wherein the flat wire is in tension between the proximal attachment location and the distal attachment location so that the flat wire coil has a reduced inner diameter, which is smaller than the rest inner diameter, between the proximal attachment location and the distal attachment location;
    wherein the flat wire coil defines a rest winding gap between adjacent turns of the flat wire coil when at rest; and
    the flat wire coil is in a compressed state between the proximal attachment location and the distal attachment location and defines a reduced winding gap, which is smaller than the rest winding gap.

8. A method of making a wire guide that includes an elongated solid core mandrel with a length, and a uniform diameter over a majority of the length; a flat wire formed into a flat wire coil that, when at rest, defines a rest inner diameter that is greater than the uniform diameter, and an entire coil length of the flat wire coil matches the length of the elongated solid core mandrel; the elongated solid core mandrel being received in the flat wire coil; the flat wire coil being attached to the elongated solid core mandrel at a distal attachment location and a proximal attachment location; the distal attachment location being closer to a distal end of the elongated solid core mandrel than to the proximal attachment location, which is closer to a proximal end of the elongated solid core mandrel than to the distal attachment location; wherein the flat wire is in tension between the proximal attachment location and the distal attachment location so that the flat wire coil has a reduced inner diameter, which is smaller than the rest inner diameter, between the proximal attachment location and the distal attachment location, the method comprising the steps of:

sliding the elongated solid core mandrel into the flat wire coil;

attaching the flat wire coil to the elongated solid core mandrel at the distal attachment location;

torquing the elongated solid core mandrel in a direction with respect to the flat wire coil that puts tension in the flat wire of the flat wire coil and reduces the inner diameter of the flat wire coil from the rest inner diameter to the reduced inner diameter;

attaching the flat wire coil to the elongated solid core mandrel at the proximal attachment location while retaining the tension in the flat wire; and the distal attachment location being closer to the distal end of the elongated solid core mandrel than to the proximal attachment location, which is closer to the proximal end of the elongated solid core mandrel than to the distal attachment location;

wherein the torquing step is performed without moving a proximal end of the flat wire coil relative to the elongated solid core mandrel along a longitudinal axis.

9. The method of claim 8 including a step of compressing the flat wire coil toward the distal attachment location prior to the attaching at the proximal attachment location.

10. The method of claim 9 wherein the torquing and compressing steps are performed at least partially simultaneously.

11. The method of claim 9 wherein a winding gap defined between two turns of the flat wire coil is reduced responsive to the compressing step.

12. The method of claim 8 wherein the step of attaching at the proximal attachment location includes positioning hot liquid solder material in a winding gap defined between two turns of the flat wire coil.

13. The method of claim 8 including measuring a torque during the torquing step; and the torquing step is stopped at a predetermined torque magnitude.

14. The method of claim 8 wherein the inner diameter of the flat wire coil is reduced responsive to the torquing step.

15. The method of claim 8 wherein an interference contact between the elongated solid core mandrel and the flat wire coil is increased responsive to the torquing step.

\* \* \* \* \*